United States Patent
Raudabough et al.

(10) Patent No.: US 7,024,968 B2
(45) Date of Patent: Apr. 11, 2006

(54) LUER LOCK WRENCH

(75) Inventors: Douglas Raudabough, Clear Lake, MN (US); Mark St. Marie, Big Lake, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 171 days.

(21) Appl. No.: 10/397,724

(22) Filed: Mar. 26, 2003

(65) Prior Publication Data

US 2004/0193145 A1 Sep. 30, 2004

(51) Int. Cl.
B25B 13/00 (2006.01)

(52) U.S. Cl. ..................................... 81/124.2; 81/121.1

(58) Field of Classification Search ................... 81/119, 81/121.1, 124.2, 3.4, 3.41, 488, 901, DIG. 7, 81/DIG. 10
See application file for complete search history.

(56) References Cited

U.S. PATENT DOCUMENTS

| | | | | |
|---|---|---|---|---|
| 1,867,372 | A | * | 7/1932 | McGuckin ................. 81/124.2 |
| 2,691,912 | A | * | 10/1954 | Jones ......................... 81/124.2 |
| 3,121,355 | A | * | 2/1964 | Morel et al. ................ 81/176.2 |
| 3,394,954 | A | | 7/1968 | Sams |
| 4,076,285 | A | | 2/1978 | Martinez |
| 4,133,312 | A | | 1/1979 | Burd |
| 4,187,848 | A | | 2/1980 | Taylor |
| 4,294,250 | A | | 10/1981 | Dennehey |
| 4,296,949 | A | | 10/1981 | Muetterties et al. |
| 4,432,766 | A | | 2/1984 | Bellotti et al. |
| 4,526,572 | A | | 7/1985 | Donnan et al. |
| 4,562,758 | A | * | 1/1986 | Stirling ...................... 81/124.4 |
| 4,636,204 | A | | 1/1987 | Christopherson et al. |
| 4,639,019 | A | | 1/1987 | Mittleman |
| 4,757,730 | A | | 7/1988 | Porat et al. |
| 4,778,447 | A | | 10/1988 | Velde et al. |
| 4,824,145 | A | | 4/1989 | Carlsson |
| 4,834,719 | A | | 5/1989 | Arenas |
| 4,845,827 | A | | 7/1989 | Vandermast et al. |
| 4,969,879 | A | | 11/1990 | Lichte |
| 5,209,740 | A | | 5/1993 | Bryant et al. |
| 5,297,458 | A | * | 3/1994 | Smith et al. ................ 81/124.3 |
| 5,312,377 | A | | 5/1994 | Dalton |
| 5,330,450 | A | | 7/1994 | Lopez |
| 5,591,143 | A | | 1/1997 | Trombley, III et al. |
| 5,651,776 | A | | 7/1997 | Appling et al. |
| 5,673,976 | A | * | 10/1997 | Hillis et al. ..................... 301/58 |
| 6,044,732 | A | * | 4/2000 | Astle ......................... 81/176.15 |
| 6,152,913 | A | | 11/2000 | Feith et al. |
| 6,319,231 | B1 | | 11/2001 | Andrulitis |
| 6,332,633 | B1 | | 12/2001 | Fitoussi et al. |
| 6,817,272 | B1 | * | 11/2004 | Holland ..................... 81/124.2 |

* cited by examiner

*Primary Examiner*—David B. Thomas
(74) *Attorney, Agent, or Firm*—Miller, Matthias & Hull

(57) ABSTRACT

A tool for aiding the locking of luer-type locks is disclosed. A luer lock connection device includes a cooperating threaded male luer lock connector and a threaded female luer lock connector each with raised portions on their respective exteriors to aid in the rotating of one of the connectors about the other to lock the two together. The disclosed tool includes a ring which surrounds the connector and a slot on the interior of the ring which engages the raised portion on the connector upon which it is disposed. The tool also includes a wing which the user employs to impart force to rotate the connector upon which the tool is disposed.

14 Claims, 2 Drawing Sheets

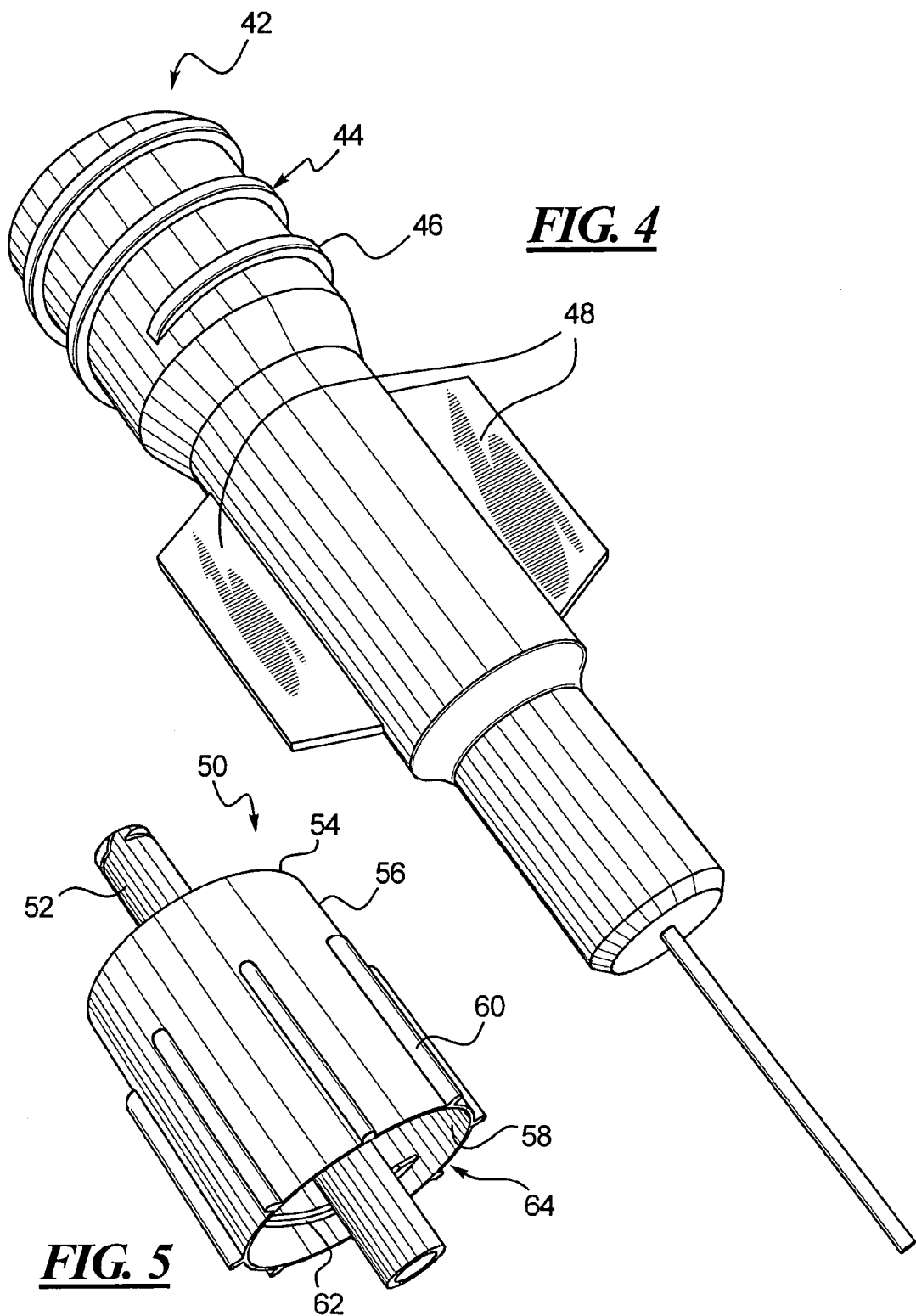

LUER LOCK WRENCH

TECHNICAL FIELD

This invention concerns a novel wrench that is particularly suited to fasten and open items connected with luer locks.

BACKGROUND OF THE RELATED ART

In medicine and related fields, it is well known to connect small tubing and instruments such as catheters or syringes using a type of lock known as a "luer lock." By connecting catheters with other instruments, a doctor is aided in the removal or addition of fluids for the patient. Luer locks typically comprise two components that are connected. In one example, the first component is fixed, and the second component is rotatable. The fixed component includes a tube with an inner surface and an outer surface, the inner surface defining a passageway through which the liquid flows. The outer surface is coaxial with the inner surface and has a threaded portion that actually performs the locking function.

The rotating component includes a hollow cylinder coaxially surrounding a smaller, protruding inner tube through which liquid flows. However, this outer cylinder of the rotating component rotates freely about the inner tube along the common axis. The outer cylinder of the rotating component is threaded on its inner surface. The inside diameter of the outer cylinder of the rotating component corresponds to the outer diameter of the outer cylinder of the fixed component. Thus, when the outer cylinder of the rotating component is rotated about the outer surface of the fixed component, the threaded portions of the two elements interlock and the threaded portions and the cylinders interact to form a liquid-tight seal.

To aid in the locking of the two elements, manufacturers often place flanges on the outer surface of the outer cylinder of the rotating component. This gives the user more leverage with which to rotate the outer cylinder to ensure that the seal between the two elements is truly liquid-tight. An example of this can be seen in U.S. Pat. No. 4,294,250.

However, environments that medical devices are put in are often wet and slick. In these situations, even luer locks with a flanged head are difficult to manipulate. Any air or airborne contaminant entering the catheter can be dangerous or potentially fatal. Thus, there is a need to be able to securely engage the two elements of a luer lock to prevent leakage. Furthermore, the difficult and repeated actions of locking and unlocking the small luer locks can have a detrimental effect on the joints and muscles of the doctor, including promoting carpal tunnel syndrome.

SUMMARY OF THE DISCLOSURE

The disclosed device is directed to a tool comprising a ring with an interior annular surface and an exterior annular surface. At least one wing is disposed on the exterior annular surface of the ring, and at least one slot is disposed on the interior annular surface of the ring.

BRIEF DESCRIPTION OF THE DRAWINGS

FIG. 4 is a perspective view of a monorail manifold with a fixed locking structure.

FIG. 5 is a perspective view of a rotating adapter with a rotating locking structure.

DETAILED DESCRIPTION

Figure 1:
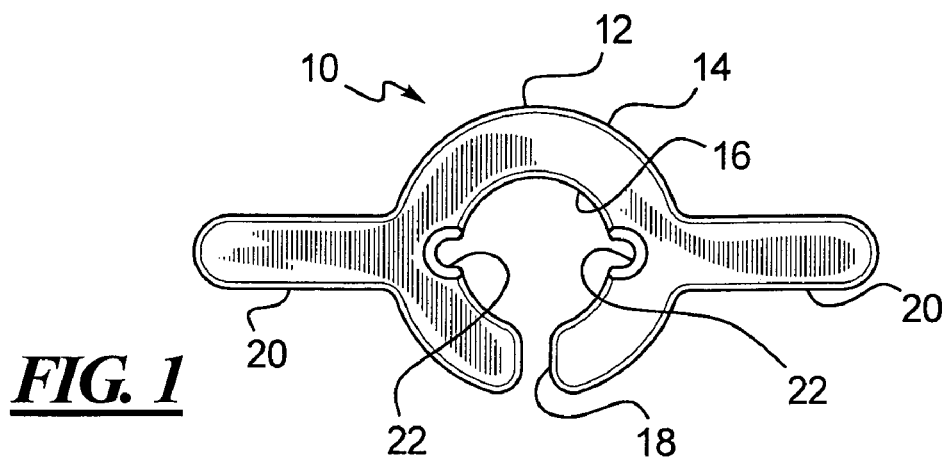
FIG. 1 is a plan view of a luer wrench constructed in accordance with the principles disclosed herein.
Figure 2:
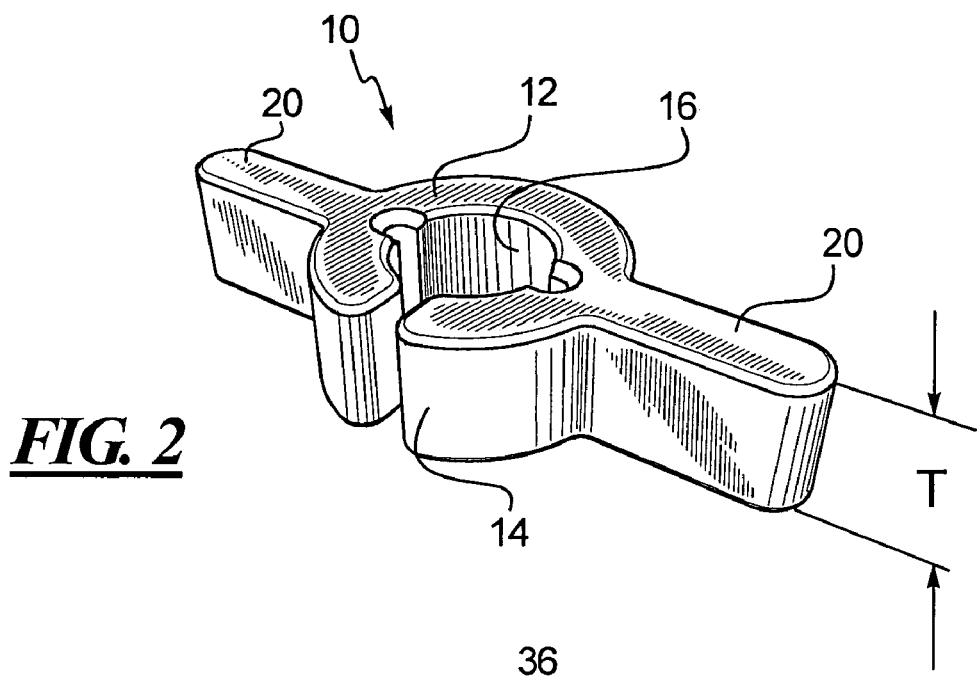
FIG. 2 is a perspective view of the wrench of FIG. 1.
Figure 3:
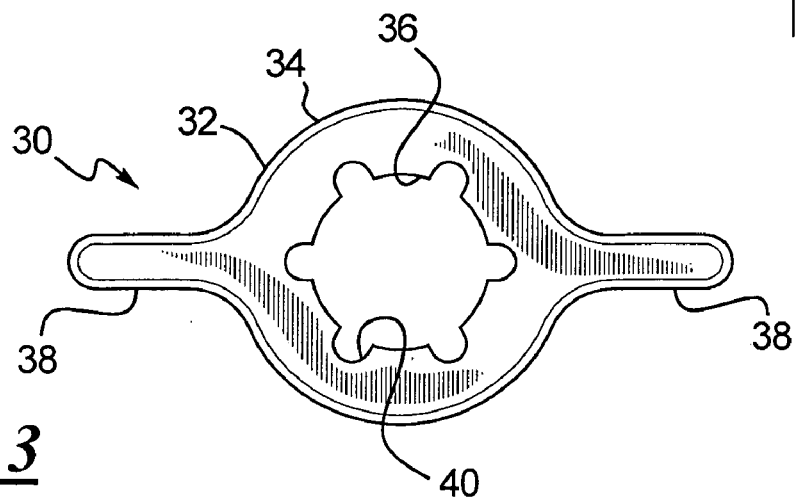
FIG. 3 is a plan view of a second example of a wrench constructed in accordance with the principles disclosed herein.

Referring now to the drawings, FIGS. 1 and 2 illustrate a tool generally depicted as reference number 10. The tool 10 comprises an annular ring 12 with an exterior surface 14 and an interior surface 16. The ring 12 may include a through slot 18. The tool 10 can be manufactured of any material that can be machined or formed into the structure as shown in FIGS. 1–3. As an example, due to their durability, low cost and ease of molding and machining, polymers such as acetal have proven to be effective.

The tool 10 also includes at least one wing 20 disposed on the ring 12. The wing 20 is used by a doctor to gain leverage on the tool to increase the torque applied by the doctor to ensure that the luer lock is securely fastened. This increased torque lowers the strain on the doctor's hands in fastening the lock, thereby helping to protect against a variety of possible physical problems, including carpal tunnel syndrome.

In the example of FIG. 1, the tool comprises two wings 20. Although these wings 20 are shown as disposed on opposite sides of the ring 12 and at a right angle to the through slot 18, it is clear that the wings can be at any angle to each other for any given reason. It may be determined that the wings 20 should be set at a certain relative angle for ergonomic reasons. Further, in a given situation, there may not be space for wings 20 on opposite sides, and as such, it may be necessary to provide the wings 20 at a smaller angle with regard to each other or even just a single wing 20.

At least one leverage slot is disposed on the interior surface 16 of the ring 12. In the example shown in FIG. 1, there are two slots 22. The slots 22 engage a luer lock connector device, examples of which are shown in FIGS. 4 and 5. Depending on the configuration of the luer lock connector, more than two slots 22 may be necessary to properly engage the luer lock connector. In the present example, the leverage slots 22 are collinear with the wings 20, although they need not be.

The tool 10 has a cross sectional thickness T. The thickness T is chosen such that it is long enough for the tool 10 to engage the luer lock connector effectively, yet short enough such that the tool 10 is easily maneuverable and not unwieldy.

A second example of a tool 30 is depicted in FIG. 3. The tool 30 includes an annular ring 32 with an exterior surface 34 and an interior surface 36. In this example, no through slot is provided.

On the exterior surface 34 of the ring 32 is disposed at least one wing 38. In the present example, two wings 38 are disclosed, however, any number of wings 38 may be disposed on the ring 32 in any angular configuration that would prove useful to the user.

Disposed on the interior surface 36 of the ring 32 is at least one leverage slot 40. In this particular example, six slots 40 are disclosed, disposed radially about the center of the ring 32. Again, in this example, two of the six slots 40 are disposed collinear with the wings 38.

Disclosed in FIGS. 4 and 5 are examples of known implements that can be used in conjunction with the tools 10 and 30 described earlier. A monorail manifold 42 is depicted in FIG. 4. The monorail manifold 42 has a fixed locking structure 44 with threads 46. Disposed on the monorail manifold 42 is a pair of flaps 48. The flaps 48 may be used to gain leverage in rotating the monorail manifold 42 by hand.

A rotating adapter 50 is shown in FIG. 5. The rotating adapter 50 is comprised of a fixed portion 52 and a rotating portion 54. The rotating portion 54 has an exterior surface 56 and an interior surface 58. Disposed on the exterior surface 56 of the rotating portion 54 are a plurality of ridges 60, in this case a total of six, which generally aid the user in grasping and rotating the rotating portion 54. Disposed on the interior surface 58 of the rotating portion 54 are raised threads 62. The raised threads 62 form a rotatable locking structure 64 in conjunction with the interior surface 58.

In practicing the disclosed example, the fixed locking structure 44 of the monorail manifold 42 is inserted into the interior surface 58 of the rotating adapter 50. Either or both of the tools 10 and 30 are then slipped over the monorail manifold 42 and the rotating adapter 50. The tools 10 and 30 can also be placed on the respective implements prior to the insertion.

In this example, the tool 10 of the first example is particularly suited to be used in conjunction with the monorail manifold 42. As such, the tool 10 is placed around the monorail manifold 42 such that the interior surface 16 surrounds the monorail manifold 42, and the leverage slots 22 of the tool 10 engage the flaps 48 of the monorail manifold 42. The tool 30 of the second example is suited to be used in conjunction with the rotating adapter 50. Again, the tool 30 is placed over the rotating adapter 50 such that the leverage slots 40 of the tool 30 engage the ridges 60 of the rotating adapter 50. In this particular example, tool 30 may also be used with the monorail manifold 42.

With the tools 10 and 30 in place on the monorail manifold 42 and rotating adapter 50, the user may then use the tools 10 and 30 to rotate the monorail manifold 42 and rotating adapter 50 with respect to each other, thus engaging the threads 46 of the monorail manifold 42 and the threads 62 of the rotating adapter 50 such that the two implements are locked together. By using the tools 10 and 30, the user is able to impart far greater torque and ensure that the structures being locked together are secure and a liquid-tight seal is formed.

Although one rotating and one fixed locking structure is disclosed, it is to be understood that the tool disclosed herein would be effective if both locking structures were fixed or both locking structures were rotatable.

Numerous modifications and alternative embodiments will be apparent to those skilled in the art in view of the foregoing description. Accordingly, this description is to be construed as illustrative only. The details of the structure may be varied substantially without departing from the spirit and scope of the disclosure, and the exclusive use of all modifications which come within the scope of the appended claims is reserved.

We claim:

1. A tool, comprising:
   a ring with an interior annular surface and an exterior annular surface;
   at least one wing disposed on the exterior annular surface of the ring; and
   more than two discrete slots disposed on the interior annular surface of the ring, each slot extending radially into the interior annular surface and there being a section of interior annular surface between any two adjacent slots.

2. The tool of claim 1, wherein the at least one wing comprises two wings.

3. The tool of claim 2, wherein the two wings are disposed on opposite sides of the ring.

4. The tool of claim 1, wherein the more than two slots are spaced apart equidistantly about the interior annular surface of the ring.

5. The tool of claim 4, wherein the at least one wing comprises two wings, and wherein the two wings are disposed on opposite sides of the ring.

6. The tool of claim 5, wherein the two wings are collinear with two of the more than two slots.

7. The tool of claim 1, wherein the more than two slots comprise six slots.

8. The tool of claim 7, wherein the at least one wing comprises two wings, and wherein the two wings are disposed on opposite sides of the ring.

9. The tool of claim 8, wherein two of the six slots are collinear with the two wings.

10. The wrench of claim 1, wherein the interior annular surface is concentric with the exterior annular surface.

11. A wrench for a luer-type lock, comprising:
    a ring with an interior annular surface and an exterior annular surface, the interior annular surface defining an opening with a generally constant cross section extending through the ring;
    two wings disposed on opposite sides of the exterior annular surface of the ring; and
    a plurality of slots disposed on the interior annular surface of the ring, each slot extending radially into the interior annular surface and there being a section of interior annular surface between any two adjacent slots.

12. The wrench of claim 11, wherein the opening includes a hole.

13. The wrench of claim 11, wherein the wrench is a single contiguous piece.

14. The wrench of claim 11, wherein the interior annular surface is concentric with the exterior annular surface.

* * * * *